(12) United States Patent
Chen et al.

(10) Patent No.: US 8,891,081 B1
(45) Date of Patent: Nov. 18, 2014

(54) RAMAN SPECTROSCOPY METHOD OF MEASURING MELAMINE CONTENTS IN DAIRY PRODUCTS HAVING DIFFERENT MATRIXES

(71) Applicants: Nuctech Company Limited, Beijing (CN); Tsinghua University, Beijing (CN)

(72) Inventors: Zhiqiang Chen, Beijing (CN); Li Zhang, Beijing (CN); Jianhong Zhang, Beijing (CN); Hongqui Wang, Beijing (CN); Ziran Zhao, Beijing (CN); Jianping Gu, Beijing (CN); Zhiming Wang, Beijing (CN); Qingping Huang, Beijing (CN); Yumin Yi, Beijing (CN)

(73) Assignees: Nuctech Company Limited, Beijing (CN); Tsinghua University, Beijing (CN)

( * ) Notice: Subject to any disclaimer, the term of this patent is extended or adjusted under 35 U.S.C. 154(b) by 0 days.

(21) Appl. No.: 14/145,454

(22) Filed: Dec. 31, 2013

(30) Foreign Application Priority Data

Apr. 28, 2013 (CN) .......................... 2013 1 0155894

(51) Int. Cl.
*G01J 3/44* (2006.01)
*G01N 21/65* (2006.01)
(52) U.S. Cl.
CPC ...................... *G01N 21/65* (2013.01)
USPC ........................................................ 356/301
(58) Field of Classification Search
USPC .............................................. 356/301, 72–73
See application file for complete search history.

(56) References Cited

U.S. PATENT DOCUMENTS

2009/0046284 A1 * 2/2009 Wang et al. .................. 356/301
2011/0207231 A1 8/2011 Natan et al.

FOREIGN PATENT DOCUMENTS

| CN | 101477051 A | 7/2009 |
| CN | 101487797 A | 7/2009 |
| CN | 102156177 A | 8/2011 |
| CN | 103149312 A | 6/2013 |

OTHER PUBLICATIONS

Liu, Feng, et al., "Development of Portable Raman Spectometer and Its Application for Determination of Melamine," *Chinese Journal of Analytical Chemistry*, Oct. 2011 (pp. 1531-1536).
Cheng, Jie, et al., "Rapid Determination of Melamine in Pet Food by Surface Enhanced Raman Spectroscopy in Combination with Ag Nanoparticles," *Spectroscopy and Spectral Analysis*, vol. 31, No. 1, Jan. 2011 (pp. 131-135).
Lu, Jie, et al., "Review of analytical methods for determining melamine in Different matrix," National Institute of Nutrition and Food Safety, China CDC, Beijing 100021, Feb. 20, 2009 (pp. 55-61).

* cited by examiner

*Primary Examiner* — Abdullahi Nur
(74) *Attorney, Agent, or Firm* — Christensen Fonder P.A.

(57) ABSTRACT

A raman spectroscopy method of measuring melamine contents in dairy products having different matrixes. The method includes: (a) establishing a database of characteristic curves of dairy products having different matrixes; (b) taking several copies of the dairy products having one certain unknown matrix and adding melamine standard solutions having different concentrations therein, to obtain a series of dairy product samples in which the relative concentrations of the melamine are known; (c) performing raman spectrum testing analysis and obtaining corresponding characteristic peak intensities to obtain a slope of the characteristic curve showing variation of the characteristic peak intensities with the relative concentrations of the melamine; (d) searching the database of step (a) using the slope of the characteristic curve of the dairy product samples to find a matching characteristic curve, and (e) calculating concentration of melamine in the dairy products by using the matched characteristic curve and the characteristic peak intensity.

10 Claims, 5 Drawing Sheets

RAMAN SPECTROSCOPY METHOD OF MEASURING MELAMINE CONTENTS IN DAIRY PRODUCTS HAVING DIFFERENT MATRIXES

CROSS-REFERENCE TO RELATED APPLICATION

This application claims the benefit of Chinese Patent Application No. 201310155894.7 filed on Apr. 28, 2013 in the State Intellectual Property Office of China, the disclosure of which is incorporated herein by reference.

BACKGROUND OF THE INVENTION

1. Field of the Invention

The present invention relates to the field of detecting melamine content in dairy products, and more particularly, to the method of detecting melamine content in dairy products having different matrixes.

2. Description of the Related Art

Chinese government-issued regulations "*Method of Detecting Melamine in Raw Milk and Dairy Products*" (GB/T 22388-2008), regulate three methods of detecting melamine in raw milk, in dairy products, and in milk contained products, i.e., high performance liquid chromatography (HPLC), liquid chromatography-mass spectrometry (LC-MS/MS), as well as gas chromatography-mass spectrometry [including GC-MS, GC-MS/MS]. Although these methods can facilitate accurate qualitative analysis and quantitative analysis, they can only be performed in labs, due to limitations such as complicated operations, harsh operating conditions, high cost of consumptive materials, and low detecting speed, or the like.

One patent application filed by the China Academy of Inspection and Quarantine has been published with a publication number of CN101477051, entitled with "Raman Spectroscopy for Quick Field Detecting Melamine in the Liquid Milk and Reagent Kit". The above described patent application discloses one method to quantitatively detect melamine contents in liquid milk using raman spectroscopy. This method mainly studied characteristic curves showing variation of characteristic peak intensity of the raman spectrum of the fresh milk with concentration of the melamine therein, and adopted such characteristic curves and the raman spectrum of the fresh milk to be detected. This can detect the melamine more quickly, and obtain a relatively good detection result with respect to the contents of the melamine in the fresh milk. However, when detecting other kinds of liquid milks, there are some differences between their characteristic curves and those of the fresh milks, since compositions of various different liquid milks will vary. If a quantitative calculation is still done with the characteristic curve of the fresh milks, then it would cause large deviation of the calculation results from the real values. Real measurement indicates that such a method will cause a relatively large measuring deviation upon detecting various liquid milks available on the market. This is mainly because the liquid milks have different compositions and these different matrixes will largely affect the measurement of the raman spectroscopy. Therefore, one of main difficulties for quantitative detection of the melamine in dairy products with raman spectroscopy is to remove interferences caused by different matrixes in the dairy products being measured.

In view of this, there is indeed a need for a quantitative analysis method for quickly and/or accurately detecting melamine content in dairy products having different matrixes.

SUMMARY OF THE INVENTION

In view of the above shortages in the prior art, an object of the present invention is to alleviate at least one aspect of the above problems and defects.

Concerning the above, one objective of the present invention is to establish a testing and data analyzing method to avoid interferences from the different matrixes in dairy products by using raman spectroscopy, and to achieve the quantitative detection of melamine in the dairy products having different matrixes by using raman spectroscopy.

In accordance with one aspect of the present invention, it provides a raman spectroscopy method of measuring melamine contents in dairy products having different matrixes, comprises the following steps:

(a) establishing a database of characteristic curves of the dairy products having different matrixes;

(b) taking several copies of dairy products to be detected having one certain unknown matrix, and adding melamine standard solutions with different concentrations into the several copies respectively, to obtain a series of such dairy product samples in which the relative concentrations of the melamine are known;

(c) performing raman spectrum testing analysis on the dairy product samples and obtaining corresponding characteristic peak intensities, so that a slope of the characteristic curve showing variation of the characteristic peak intensities of the dairy product samples with the relative concentrations of the melamine is obtained;

(d) carrying out a search in the database established in the step (a) by using the slope of the characteristic curve of the dairy product samples, so as to find a characteristic curve matched with it; and (e) calculating concentration of the melamine in the dairy products to be detected by using the matched characteristic curve and the characteristic peak intensity of the dairy product to be detected.

Further, in the step (b), after adding the melamine standard solutions into the dairy products to be detected, a water, an organic solvent or a salt is added into the dairy product to be detected, and then they are uniformly mixed, centrifugally treated, and finally, a clear liquid thereof is taken to be ready for measurement.

In addition, a nanomaterial reinforcing agent is added into the clear liquid, and uniformly mixed with the clear liquid to form the dairy product samples.

In another embodiment, in step (c), the process of obtaining the characteristic peak intensity further comprises:

performing background subtraction processing on the obtained raman spectrum of the dairy product sample, in order to obtain a smooth raman spectrum;

obtaining the characteristic peak intensity of the characteristic peak, by dividing a corresponding peak area at a raman shift of a first characteristic peak in the raman spectrum by a corresponding peak area at a raman shift of a second characteristic peak.

Specifically, the raman shift of the first characteristic peak is approximately 707 $cm^{-1}$; and the raman shift of the second characteristic peak is approximately 935 $cm^{-1}$.

In a further embodiment, step (a) includes measuring the concentrations of the melamine in a series of the dairy product samples having the same matrix, by means of high performance liquid chromatography, liquid chromatography-mass spectrometry, or gas chromatography-mass spectrometry;

obtaining characteristic peak intensities of the dairy product samples having the same matrix by raman spectroscopy, so that a characteristic curve showing variations of the characteristic peak intensities of the dairy product having such matrix with the melamine concentration is established; and establishing a database of the characteristic curves of the dairy products having different matrixes, by measuring the characteristic curves of the dairy products having different matrixes.

In an embodiment, the water comprises deionized water, or distilled water; the organic solvent comprises alcohol or acetone, and the salt comprises kalium chloride, or sodium chloride.

In an embodiment, the nanomaterial reinforcing agent comprises any one of metal nanoparticles, metal nanowires, metal nanoclusters, carbon nanotubes, carbon nanoparticles, or a combination thereof, with a size in the range of 1-1000 nm.

In an embodiment, the metal comprises any one of gold, silver, copper, magnesium, aluminium, iron, cobalt, nickel, palladium, and platinum, or a combination thereof.

In one further embodiment, in step (c), the slope of the characteristic curve is determined based on the differential method or linear fitting method, in accordance with variation of the characteristic peak intensities with the concentrations of the melamine.

BRIEF DESCRIPTION OF THE DRAWINGS

These and other aspects and advantages of the present invention can become apparent and readily understood from the description of the preferred embodiments in combination with the accompanying figures below.

DETAILED DESCRIPTION OF THE INVENTION

Technical solutions of the present invention will be described hereinafter in more detail by the way of embodiments with reference to accompanying drawings, wherein the same or like reference numerals refer to the same or like elements throughout the specification. The explanation of the embodiments of the present invention with reference to the accompanying drawings is intended to interpret the general inventive concept of the present invention, rather than being construed as limiting the present invention.

The main concept of the present invention is: performing raman spectroscopy measurement and analysis of dairy products having the same matrix, with known concentration of melamine; establishing characteristic curves of the corresponding raman spectroscopy peak intensities vs. the melamine concentrations of the dairy products having the same matrix; studying and analyzing the characteristic curves of the corresponding raman spectroscopy peak intensities vs. the melamine concentrations of the dairy products having a plurality of different matrixes, so as to establish a database of the characteristic curves; performing a plurality of raman spectroscopy measurements of the dairy product to be detected by using relative methods, so as to determine a slope of the characteristic curve; establishing the characteristic curve of the dairy product to be detected in combination with the database; and using the obtained characteristic curve to calculate the contents of the melamine in the dairy products to be detected.

A raman spectroscopy method of detecting a content of melamine in dairy products having different matrixes in accordance with the present invention, comprises the following steps:

1) Preparation of samples having known melamine concentrations: the concentration of the melamine in the dairy products can be measured by means of the above described national standard measuring method (for example, HPLC, LC-MS/MS, GC-MS, GC-MS/MS); a series of samples having known melamine concentrations can be obtained by adding melamine standard solutions having different concentrations.

2) Raman spectroscopy measurement: after taking a certain amount of samples, a certain amount of water, or chemicals such as organic solvents, salts or the like can be added into the samples. After uniformly mixing, a centrifugal treatment is performed and the obtained clear liquid is ready for detection. A certain amount of the clear liquid is mixed with one nanomaterial reinforcing agent, and the raman spectrum of the obtained mixture can be measured by a raman spectrometer.

3) analysis of characteristic peak intensities: obtaining a characteristic peak intensity of one certain characteristic peak in the raman spectrum, i.e., a relative intensity of a signal (or peak area) at a raman shift of the certain characteristic peak with respect to a signal (or peak area) at a raman shift of another characteristic peak.

Figure 1:
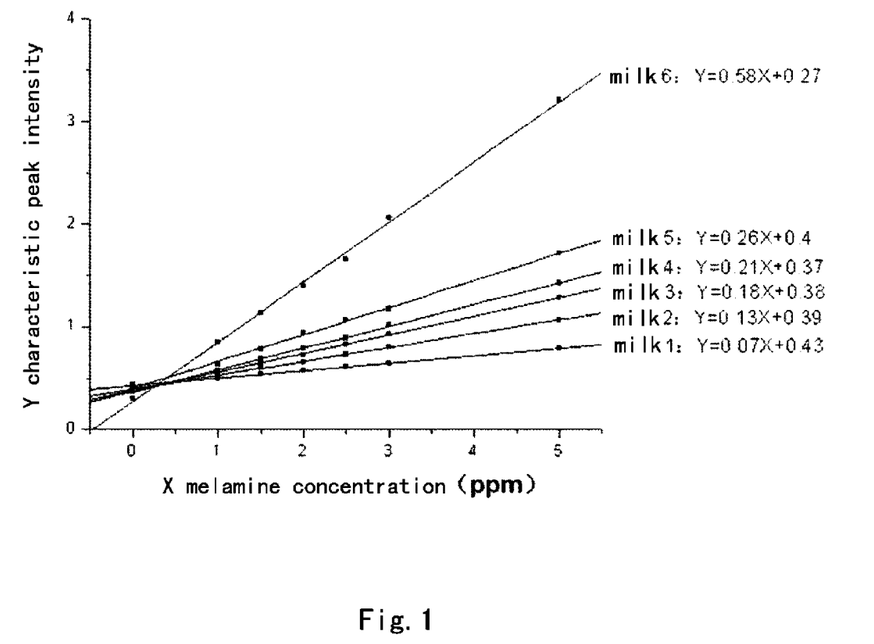
FIG. 1 is a schematic view showing a part of an established database including characteristic curves of the dairy products having different matrixes in accordance with an embodiment of the present invention.
Figure 2A:
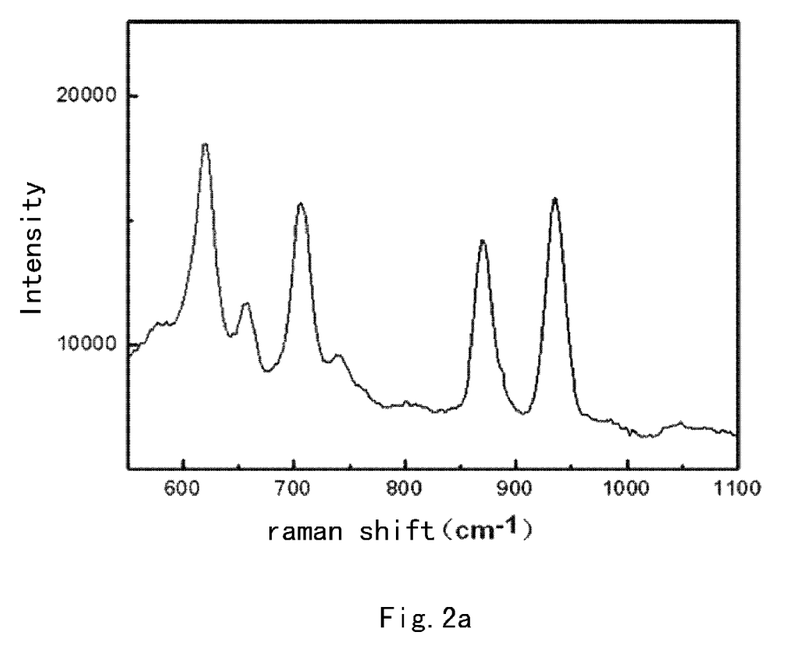
FIGS. 2a-2c are views of raman spectra for three liquid milk samples detected by a method in accordance with an embodiment of the present invention, wherein the liquid milk samples each are formed by adding melamine standard solutions with different concentrations into the liquid milk having a certain matrix.
Figure 2B:
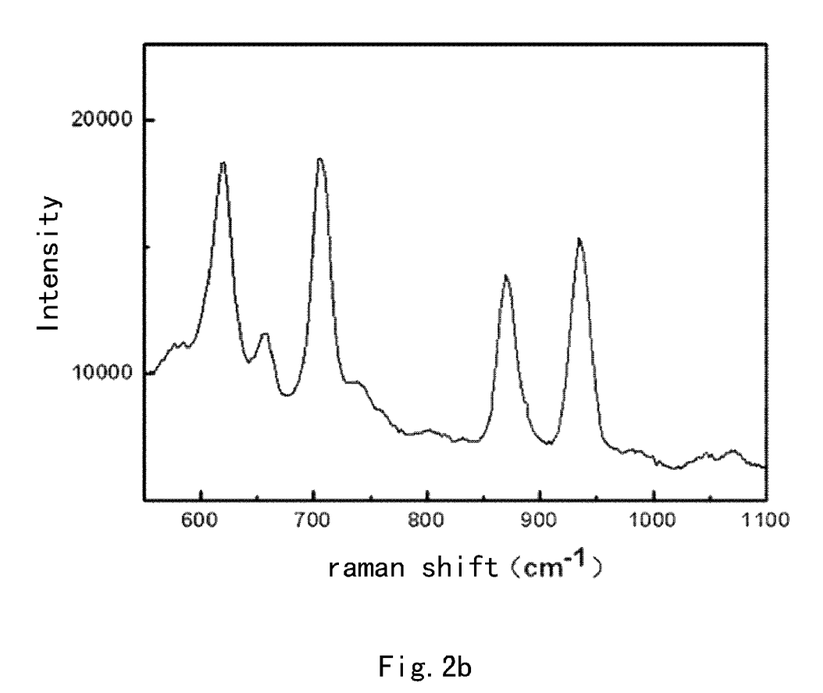
Figure 2C:
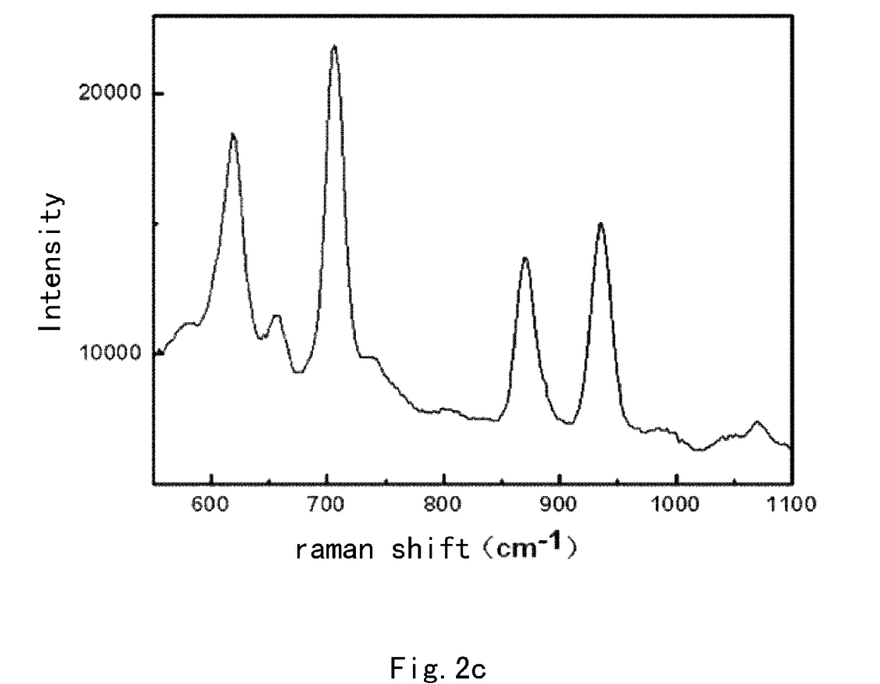
Figure 3:
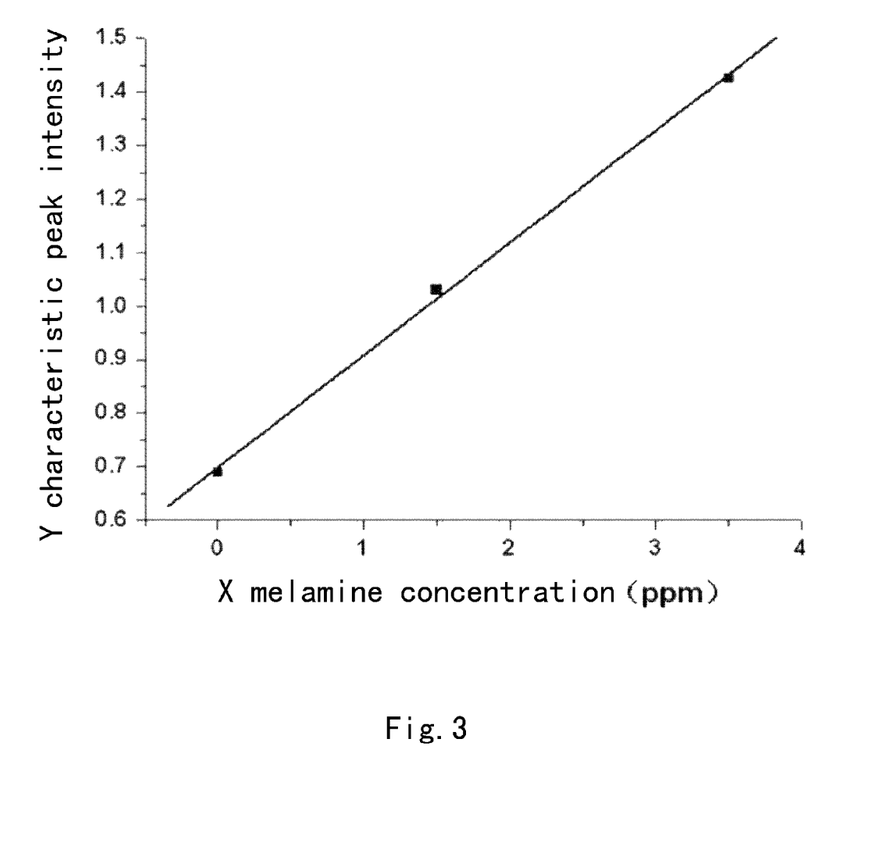
FIG. 3 is a schematic view showing characteristic curves of the liquid samples to be detected as shown in FIGS. 2a-2c, obtained by calculation in the present invention.

4) establishing characteristic curve: as for the dairy products having the same matrix, establishing the characteristic curve showing variation of the characteristic peak intensities with the concentration changes of the melamine;

5) establishing database: with respect to the dairy products having different matrixes, the corresponding characteristic curves are established, so as to constitute the corresponding database (as shown in FIG. 1, the zero point or 0 ppm of the melamine concentration as shown in FIG. 1 indicates the milk sample is really free of melamine);

6) relative measurement: after taking multiple samples of the dairy product to be detected, and respectively adding melamine standard solutions with different concentrations into the samples, a series of samples of the dairy product to be detected having different matrixes can be obtained wherein the relative concentrations of the melamine have been known, and in accordance with the step 2), the raman spectrum (as shown in FIGS. 2a-2c) of each sample to be detected can be measured and then the characteristic peak intensities thereof are obtained;

7) Quantitative analysis: the characteristic curve corresponding to the dairy product to be detected can be established by using the database established by the step 5) and the characteristic peak intensities of the raman spectrum obtained by the relative measurement in the step 6) (see FIG. 3). In combination with the characteristic curve and the characteristic intensities of the raman spectrum of the sample to be detected, the concentration of the melamine in the sample can be quantitatively calculated.

With the above relative measurement and data analysis method as described, the quantitative measurement to the melamine contents in the dairy products can be achieved. When the content of the melamine is above 2.5 mg/kg, the detection rate of recovery is 80%~110%, and the relative standard deviation is less than 10%.

In the present invention, the step of establishing the database consisting of the characteristic curves of the dairy products having different matrixes specifically comprises: the concentrations of the melamine in a series of dairy product samples having the same matrix are measured by the method regulated by the national government, such as HPLC, LC-MS/MS, GC-MS and GC-MS/MS; the characteristic peak intensities of the above samples are obtained by the raman spectroscopy, so that the characteristic curve showing variation of the characteristic peak intensities of the dairy product having the same matrix with the concentration of the melamine is established; and then by detecting and obtaining the characteristic curves of the dairy products having different matrixes, the database of the characteristic curves for the dairy products having different matrixes can be established.

In an embodiment of the present invention, the nanomaterial reinforcing agent applied in the step 2) may include any one of metal nanoparticles, nanowires, nanoclusters, carbon nanotubes, carbon nanoparticles, or a combination thereof with the size in the range of 1-1000 nm. The metal nanoparticles, nanowires, or nanoclusters include the nanoparticles, nanowires, or nanocluster made of any one of gold, silver, copper, magnesium, aluminium, iron, cobalt, nickel, palladium, and platinum, or a combination thereof.

In addition, in step 2), the water may include deionized water, or distilled water; and the organic solvent includes alcohol or acetone, or the like, the salt may include kalium chloride, or sodium chloride, and so on.

In step 3), the process of obtaining the characteristic peak intensities may include: performing background subtraction processing on the obtained raman spectrum of the dairy product sample in order to obtain a smooth raman spectrum; obtaining a characteristic peak intensity of the characteristic peak, by dividing a corresponding peak area at a raman shift of a first characteristic peak in the raman spectrum by a corresponding peak area at a raman shift of second characteristic peak. In an embodiment, the raman shift of the first characteristic peak is approximately 707 $cm^{-1}$; and the raman shift of the second characteristic peak is approximately 935 $cm^{-1}$.

In an example of the present invention, the process of obtaining the slope of the characteristic curve is as follows: the slope of the characteristic curve is determined by a differential method or linear fitting method, based on variation of the characteristic peak intensities with the concentrations of the melamine.

As compared with the method mentioned in the regulations of "GB/T 22388-2008", the present invention obtains the following advantages, such as simple pre-processing of the samples, low cost of the consumable materials for testing, and quick field detection. With respect to other raman spectroscopy reported in the prior art, the biggest advantage of the present invention removes the interferences of the detection with the matrixes. The present method is not limited to detection of one certain dairy product, but can be applied to more than 20 kinds of liquid dairy products sold in the current market. It can achieve the quantitative detection, the measuring limit of 2.5 mg/kg, and good repetition (quantitative analysis, RSD≤10%).

In an embodiment, a method of the present invention includes:

Step 1: a plurality of copies of 500 μL liquid milk having known melamine concentrations are put into a plurality of centrifuge tubes respectively. And then, one of 50 μL melamine standard solutions having different concentrations and 800 μL absolute ethyl alcohol are added into each of the centrifuge tubes. After whirling 10 seconds, the tube is placed within a centrifugal machine. After being in centrifuge treatment for 12 minutes under the rotation speed of 14000 rpm, the clear liquid in an upper layer is taken and ready for detection.

Step 2: a 430 μL solution containing nano silver reinforcing agent (the concentration thereof may be 100 mg/L, and the nano silver materials or particles may have sizes in the range of 30-150 nm) and the clear liquid of milk of 200 μL as described above are added into a test bottle, and they are evenly mixed by whirling.

Step 3: a raman spectrometer having a laser light source with an emitting wavelength of 785 nm as shown in the prior art, is used to detect the raman spectrum of the mixed solution, wherein the laser power is 450 w, the integration time is 1 s, an average spectrum is obtained by continually scanning at 15 times.

Step 4: the characteristic peak intensity, i.e., the relative intensity of the raman signal of the characteristic peak at the raman shift of approximately 707 $cm^{-1}$, is obtained by dividing the peak area of the corresponding peak at a raman shift of 707 $cm^{-1}$ of the characteristic peak by the peak area of the corresponding peak at a raman shift of 935 $cm^{-1}$ of the characteristic peak.

Step 5: with respect to the liquid milk samples having different melamine contents, the characteristic curve showing a linear relationship of the relative intensity of the characteristic peak at the raman shift of approximately 707 $cm^{-1}$ with the concentration of the melamine is established.

Step 6: with respect to the liquid milk samples having different matrixes, the characteristic curves thereof are established respectively, thereby constituting a database of the characteristic curves of the liquid milks having different matrixes. FIG. 1 depicts the characteristic curves showing variation of the raman characteristic peak intensities of six liquid milks having different matrixes (for example, milks 1-6) with the concentration of the melamine.

Step 7: firstly, taking out several copies of the liquid milk having a certain unknown matrix, and then adding different concentrations of the melamine standard solutions into it, finally obtaining a series of the liquid milk samples to be detected having the certain unknown matrix, the relative concentration of the melamine therein being known.

Specifically, in the present embodiment, three copies of the liquid milk of 500 μL may be taken, and 50 μL water, 15 ppm melamine standard solution and 35 ppm melamine standard solution may be added into the three copies respectively, in the same manner as discussed in steps 1 and 2 for preparing the liquid milk samples to be detected (that is, the liquid milks having the known melamine concentrations in steps 1 and 2 are replaced by equal volumes of the liquid milks to be detected, while keeping other parameters, conditions or processing orders constant). Assuming the melamine concentration of the liquid milk to be detected is X, the melamine concentrations of the three samples are considered as X, X+1.5 ppm, X+3.5 ppm.

Step 8: With respect to the slope of the characteristic curve of the liquid milk to be detected, a search is performed within the established database, so as to find the characteristic curve matched with it.

Specifically, the raman spectrum of each sample to be detected is measured by the methods as described in the above steps, thereby obtaining the characteristic peak intensity, and the characteristic curve of the liquid milk to be detected. See FIGS. 2a-2c which illustrate the raman spectra showing the raman peak intensity and raman shift of the liquid milk to be detected.

By using the corresponding method as described in step 3, the raman spectra of the three liquid milk samples to be detected are obtained, as shown in FIGS. 2a, 2b, 2c. The calculated characteristic peak intensities (the relative intensity of the raman signal at the characteristic peak raman shift of 707 $cm^{-1}$) are respectively 0.691, 1.030, 1.426, thereby obtaining the corresponding relationship between the melamine concentration and the characteristic peak intensity, as shown in Table 1:

TABLE 1 showing the relationship between the relative concentrations of the melamine in the liquid milk to be detected and the characteristic peak intensity thereof

| Sample number | Relative concentration of the melamine (ppm) | Characteristic peak intensity |
|---|---|---|
| Sample 1 | X | 0.691 |
| Sample 2 | X + 1.5 | 1.030 |
| Sample 3 | X + 3.5 | 1.426 |

The slope of the corresponding characteristic curve is calculated by using the relative concentration of the melamine and the characteristic peak intensity. The value of X can be supposed as any value, and a linear fitting method is applied to the above three sets of data (the fitted curve of FIG. 3 is obtained in the case of X=0). After such fitting, the obtained slope is 0.21. After searching in the database for the corresponding slope, the corresponding characteristic curve is y=0.21x+0.37.

Step 9: The concentration of the melamine in the liquid milk to be detected is calculated quantitatively by using the characteristic curve and the characteristic peak intensity of the raman spectrum of the liquid milk to be detected. The characteristic peak intensity of the liquid milk to be detected is: Y=0.691. By using the characteristic curve, the melamine concentration of the liquid milk sample to be detected is calculated as 1.53 ppm. By comparison, it is found that the calculated value (by the above method) is very close to the actually measured value of 1.50 ppm (which is measured by the detection method regulated by the National Rule of Law as described above).

By measuring the samples in accordance with the above method, it is found that when the melamine content is less than or equal to 2.5-5 ppm, the recovery rate is within 80%-110%, and the relative standard deviation is less than 10%. With respect to step 7, as such, several samples of the liquid milks having unknown matrixes in which the relative concentration of the melamine is known, can be measured, so as to determine the melamine concentration in the liquid dairy products having unknown matrixes.

Although some embodiments of the general inventive concept are illustrated and explained, it will be appreciated by those skilled in the art that modifications and variations may be made in these embodiments without departing from the principles and spirit of the general inventive concept of the disclosure, the scope of which is defined in the appended claims and their equivalents.

What is claimed is:

1. A Raman spectroscopy method of measuring melamine contents in dairy products having different matrixes, comprising the following steps:
    (a) establishing a database of characteristic curves of the dairy products having different matrixes;
    (b) taking several copies of dairy products to be detected having a certain unknown matrix, and adding melamine standard solutions having different concentrations into the several copies respectively, to obtain a series of such dairy product samples in which the relative concentrations of the melamine are known;
    (c) performing Raman spectrum testing analysis on the dairy product samples and obtaining corresponding characteristic peak intensities, so that a slope of the characteristic curve showing variation of the characteristic peak intensities of the dairy product samples with the relative concentrations of the melamine is obtained;
    (d) carrying out a search in the database established in the step (a) by using the slope of the characteristic curve of the dairy product samples, so as to find out a characteristic curve matched with it; and
    (e) calculating concentration of the melamine in the dairy products to be detected by using the matched characteristic curve and the characteristic peak intensity of the dairy product to be detected.

2. The Raman spectroscopy method of claim 1, wherein, in step (b), after adding the melamine standard solutions into the dairy products to be detected, a water, an organic solvent or a salt is added into the dairy products to be detected, and then they are uniformly mixed, centrifugally treated, and finally a clear liquid thereof is taken to be ready for measurement.

3. The Raman spectroscopy method of claim 2, wherein, a nanomaterial reinforcing agent is added into the clear liquid, and uniformly mixed with the clear liquid to form the sample of the dairy products.

4. The Raman spectroscopy method of claim 1, wherein, in step (c), the process of obtaining the characteristic peak intensity further comprises:
    performing background subtraction processing on the obtained raman spectrum of the dairy product sample, in order to obtain a smooth raman spectrum;
    obtaining the characteristic peak intensity of the characteristic peak, by dividing a corresponding peak area at a raman shift of a first characteristic peak in the raman spectrum by a corresponding peak area at a raman shift of a second characteristic peak.

5. The Raman spectroscopy method of claim 4, wherein, the raman shift of the first characteristic peak is approximately 707 $cm^{-1}$; and the raman shift of the second characteristic peak is approximately 935 $cm^{-1}$.

6. The Raman spectroscopy method of claim 1, wherein, step (a) includes measuring the concentrations of the melamine in a series of the dairy product samples having the same matrix using high performance liquid chromatography, liquid chromatography-mass spectrometry, or gas chromatography-mass spectrometry;
    obtaining characteristic peak intensities of the dairy product samples having the same matrix by Raman spectroscopy, so that a characteristic curve showing variation of the characteristic peak intensities of the dairy product having such matrix with the melamine concentration is established; and establishing a database of the characteristic curves of the dairy products having different matrixes, by measuring the characteristic curves of the dairy products having different matrixes.

7. The Raman spectroscopy method of claim 2, wherein, the water comprises deionized water, or distilled water; the organic solvent comprises alcohol or acetone, and the salt comprises kalium chloride, or sodium chloride.

8. The Raman spectroscopy method of claim 3, wherein, the nanomaterial reinforcing agent comprises any one of metal nanoparticles, metal nanowires, metal nanoclusters, carbon nanotubes, carbon nanoparticles, or a combination thereof with a size in the range of 1-1000 nm.

9. The Raman spectroscopy method of claim 8, wherein, the metal comprises any one of gold, silver, copper, magnesium, aluminium, iron, cobalt, nickel, palladium, and platinum, or a combination thereof.

10. The Raman spectroscopy method of claim 1, wherein, in step (c), the slope of the characteristic curve is determined based on a differential method or linear fitting method, in accordance with variation of the characteristic peak intensities with the concentrations of the melamine.

\* \* \* \* \*